(12) United States Patent
Paseman et al.

(10) Patent No.: US 11,134,730 B1
(45) Date of Patent: Oct. 5, 2021

(54) CUSHION INCLUDING FLEXIBLE PROJECTIONS FOR LOW FORCE SEALING APPLICATIONS

(71) Applicant: FTM Corporation, Walnut, CA (US)

(72) Inventors: Sabrina Paseman, Walnut, CA (US); William G. Paseman, Walnut, CA (US)

(73) Assignee: FTM Corporation, Walnut, CA (US)

( * ) Notice: Subject to any disclaimer, the term of this patent is extended or adjusted under 35 U.S.C. 154(b) by 0 days.

(21) Appl. No.: 17/146,851

(22) Filed: Jan. 12, 2021

Related U.S. Application Data (60) Provisional application No. 63/040,972, filed on Jun. 18, 2020.

(51) Int. Cl.
    *A41D 13/11*     (2006.01)
    *A61M 16/06*     (2006.01)
    (Continued)

(52) U.S. Cl.
    CPC ...... *A41D 13/1161* (2013.01); *A41D 13/1107* (2013.01); *A61M 16/0605* (2014.02); *A62B 9/04* (2013.01); *A62B 23/025* (2013.01)

(58) Field of Classification Search
    CPC ............... A61M 16/06; A61M 16/0605; A61M 16/0611; A61M 16/0616; A61M 16/0622;
(Continued)

(56) References Cited

U.S. PATENT DOCUMENTS

| | | |
|---|---|---|
| 695,403 A | 3/1902 | Longden |
| 1,925,764 A | 9/1933 | Le Duc |

(Continued)

FOREIGN PATENT DOCUMENTS

| | | |
|---|---|---|
| AU | 2016204360 A1 | 7/2016 |
| CN | 111248536 A | 6/2020 |

(Continued)

OTHER PUBLICATIONS

Teknor Apex, "Shore Hardness and Soft TPEs", dated Sep. 20, 2017; retrieved from https://www.teknorapex.com/thermoplastic-elastomers-and-measuring-shore-hardness-chart (Year: 2017).*

(Continued)

*Primary Examiner* — Joseph D. Boecker
(74) *Attorney, Agent, or Firm* — White & Case LLP (57) ABSTRACT

A cushion used for uniform compression of a surface with varied topography with minimal stress concentrations. The cushion includes a shaped base and a plurality of flexible projections extending from the shaped base. Each of the plurality of projections has a proximal end attached to the shaped base, a distal end opposite the shaped base, and an axial section extending between the proximal and distal ends. The plurality of flexible projections can individually flex. In an aspect, a facial cushion for use with a mask brace that secures a face mask to a patient's face includes a shaped base and a plurality of flexible projections extending from the shaped base. The individually flexing projections provide greater comfort to a wearer of the mask brace because the flexible projections can conform to the structure of the wearer's face while still providing a seal of the face mask to the face.

29 Claims, 4 Drawing Sheets

(51) Int. Cl.
*A62B 9/04* (2006.01)
*A62B 23/02* (2006.01)

(58) Field of Classification Search
CPC .......... A61M 16/0627; A61M 16/0633; A61M 16/0683; A61M 2016/0661; A62B 18/02; A62B 18/025; A62B 18/084; A41D 13/11; A41D 13/1107; A41D 13/1161
See application file for complete search history.

(56) References Cited

U.S. PATENT DOCUMENTS

| | | | |
|---|---|---|---|
| 2,353,643 A | | 7/1944 | Bulbulian |
| 3,768,100 A | * | 10/1973 | Colman ............. A41D 13/1161 2/9 |
| 4,520,509 A | | 6/1985 | Ward |
| 4,688,566 A | | 8/1987 | Boyce |
| 6,062,220 A | | 5/2000 | Whitaker et al. |
| 6,338,342 B1 | * | 1/2002 | Fecteau ................ A62B 18/084 128/207.11 |
| 6,422,238 B1 | | 7/2002 | Lithgow |
| 6,766,536 B1 | | 7/2004 | Aarons |
| 7,000,252 B1 | | 2/2006 | Tobin |
| 8,042,543 B2 | | 10/2011 | Amarasinghe et al. |
| 9,056,178 B2 | | 6/2015 | McAuley et al. |
| 9,156,532 B2 | | 10/2015 | Shiue |
| 9,663,204 B2 | | 5/2017 | Kuroda |
| 9,878,118 B2 | | 1/2018 | Formica et al. |
| 10,264,834 B2 | | 4/2019 | Aihara et al. |
| 10,674,776 B2 | | 6/2020 | Matich |
| 10,702,667 B2 | | 7/2020 | Chodkowski et al. |
| 10,722,673 B2 | | 7/2020 | Kooij et al. |
| 2005/0144703 A1 | | 7/2005 | Hilbert |
| 2006/0060200 A1 | * | 3/2006 | Ho ..................... A61M 16/0683 128/206.24 |
| 2006/0117469 A1 | | 6/2006 | Garofalo et al. |
| 2008/0099022 A1 | | 5/2008 | Gebrewold et al. |
| 2008/0113143 A1 | | 5/2008 | Taylor |
| 2009/0255542 A1 | * | 10/2009 | Ugai .................... A62B 23/025 128/863 |
| 2010/0024811 A1 | * | 2/2010 | Henry ............... A61M 16/0633 128/202.16 |
| 2010/0154798 A1 | * | 6/2010 | Henry ................. A61M 16/065 128/206.24 |
| 2010/0319700 A1 | * | 12/2010 | Ng .................... A61M 16/0683 128/206.28 |
| 2011/0083670 A1 | | 4/2011 | Walacavage |
| 2011/0094515 A1 | | 4/2011 | Duffy |
| 2011/0290253 A1 | * | 12/2011 | McAuley .......... A61M 16/0622 128/205.25 |
| 2012/0180181 A1 | | 7/2012 | Best et al. |
| 2012/0204879 A1 | * | 8/2012 | Cariola ............. A61M 16/0655 128/206.24 |
| 2013/0042871 A1 | * | 2/2013 | Chang .................. A61M 16/06 128/205.25 |
| 2013/0263859 A1 | * | 10/2013 | Ho .................... A61M 16/0683 128/206.21 |
| 2013/0306077 A1 | | 11/2013 | Greenberg |
| 2014/0166019 A1 | | 6/2014 | Ho et al. |
| 2015/0101617 A1 | | 4/2015 | Duffy |
| 2015/0283348 A1 | * | 10/2015 | Harp ................. A61M 16/0683 128/205.25 |
| 2016/0067441 A1 | | 3/2016 | Bearne et al. |
| 2017/0274167 A1 | | 9/2017 | Huddart et al. |
| 2017/0354191 A1 | | 12/2017 | Maring |
| 2019/0151590 A1 | | 5/2019 | Guney et al. |
| 2019/0269183 A1 | | 9/2019 | Qu et al. |
| 2020/0030556 A1 | | 1/2020 | Olsen et al. |
| 2020/0353296 A1 | | 11/2020 | Crenshaw et al. |
| 2021/0145087 A1 | * | 5/2021 | Park ....................... A45D 44/22 |

FOREIGN PATENT DOCUMENTS

| | | |
|---|---|---|
| JP | 2013-188281 A | 9/2013 |
| KR | 20180106787 A | 10/2018 |
| WO | 2008030831 A2 | 3/2008 |
| WO | WO-2016054692 A2 | 4/2016 |
| WO | WO-2017091920 A1 | 6/2017 |

OTHER PUBLICATIONS

International Search Report and Written Opinion for PCT/US2021/025801 dated Jul. 17, 2021 (19 pages).

* cited by examiner

CUSHION INCLUDING FLEXIBLE PROJECTIONS FOR LOW FORCE SEALING APPLICATIONS

CROSS-REFERENCE TO RELATED APPLICATIONS

This application claims priority to U.S. provisional application No. 63/040,972, filed Jun. 18, 2020 which is hereby incorporated herein by reference in its entirety.

BACKGROUND

Face masks and filtration devices are extremely important as personal protective equipment in various medical settings. Face mask filtration devices protect medical professionals from contact with and inhalation of hazardous substances or disease pathogens that may be spread by excretions, secretions, or through the air. Filtration devices are also used in non-medical environments (such as areas affected by wildfires) to prevent inhalation of hazardous or undesirable substances.

Mask fit is important in preventing airborne pathogens or other hazardous materials from exiting the mask or from getting around the mask to the protected mouth and nose area. Areas not covered by the mask may be exposed to the pathogen or hazardous substance, and anywhere that the mask gapes or does not closely fit the contours of the wearer's face such pathogens or hazardous substances may enter, particularly if the pathogens are airborne. Even a well-fitting mask may show gaps or gape when the wearer speaks or when the wearer moves their head or looks down. When the face mask is not worn or fitted properly and includes gaps around the edges, the breathed air may not pass through the filtration media, or through the mask at all, before being inhaled by the wearer. Instead, the breathed air may flow around the mask at the gaps and under the mask before being inhaled. Similarly, masks which include gaps around the edges may not force exhaled air through the filtration media, and pathogens may escape from the wearer's mouth and nose around the edges of the mask.

Poorly fitting face masks put the wearer, and those around them, at risk of infection or contamination with hazardous substances and disease pathogens. Unfortunately, it can be difficult to achieve a proper fit of a face mask due to complicated designs, lack of proper training, or size issues. This leaves medical professionals, and other individuals in need of breathing air filtration through the mask, at risk of injury and illness.

Face masks can be secured to a wearer's face through the use of a mask brace. The mask brace can be formed as an elastomeric gasket forming a perimeter that surrounds the wearer's mouth, nose, and chin, with a securing strap that holds the brace on the patient's face to form a seal. The mask brace can be worn over a face mask in order to better seal the face mask to the wearer's face to prevent breathed air from escaping around the mask sides and pathogens from entering around the sides of the mask.

In order to provide an adequate seal on the wearer's face, the securing strap of the mask brace needs to apply significant force on the gasket. The force can be distributed over the face of the wearer by the shape and positioning of the mask. However, the force on the facial bones of the wearer, including the nose, cheekbones, and jaw can be uncomfortable, especially over long periods of wear. The discomfort may lead to wearer's frequent removal or adjustment of the brace and mask risking exposure of the wearer to pathogens.

The use of one or more cushions between the brace and the mask can help to assuage the discomfort caused by the force applied by the brace to the facial bones, but can lead to leakage or lack of seal at the edges of the cushions. Further, the variety of face shapes and sizes of mask wearers makes the determination of an appropriate, safe and comfortable cushion shape and size difficult.

In view of the above, there is a long-felt need to produce a comfortable cushion that can maintain a seal of a face mask brace on a variety of face sizes and shapes.

SUMMARY

In an aspect, a facial cushion for use with a mask brace that secures a face mask to a patient's face includes a shaped base and a plurality of flexible projections extending from the shaped base. Each of the plurality of projections has a proximal end attached to the shaped base, a distal end opposite the shaped base, and an axial section extending between the proximal and distal ends. The plurality of flexible projections can individually flex. The individually flexing projections provide greater comfort to a wearer of the mask brace because the flexible projections can conform to the structure of the wearer's face while still providing a seal of the face mask to the face.

In some implementations, each flexible projection is formed in a vertical plane extending from the shaped base. The flexible projection can extend from one edge of the shaped base to the opposite edge, and may be parallel to one another. In some implementations, each flexible projection is spaced apart from a neighboring flexible projection.

In some implementations, each flexible projection is formed as a column extending from the shaped base, where the flexible projections are arranged in a grid-type pattern on the shaped base. The grid-type arrangement allows the flexible projections to provide a continuous seal of the face mask on the face when the flexible projections are bent to conform to the wearer's facial topography.

In some implementations, the distal end of each flexible projection is contoured. The contour may enable a better fit to underlying facial topography. Each distal end may have a different contour, or may be angled, curved, or rounded. The contour may be symmetric across a center line of the shaped base, depending on the facial structure the cushion is designed to cover.

In some implementations, the proximal end of each of the plurality of flexible projections has a cross section that is circular, triangular, or rectangular. In some implementations, the axial section has a constant cross-section from the shaped base to the distal end. In some implementations, the axial section has a variable cross-section from the shaped base to the distal end. In some implementations, the axial section decreases in cross-section from the shaped base to the distal end.

In some implementations, the cushion is positioned on the mask brace over a nose portion, a cheek bone portion, or a jaw bone portion. The cushion may be appropriately shaped for any of these facial areas, for example the cushion may be rectangular, oval, triangular, or arch-shaped, or may have any other suitable shape. The cushion distributes force applied by the mask brace over a larger area of the wearer's face and provides a softer interface than the mask brace alone. The flexible projections are able to bend individually to provide a better fit to individual facial structures and sizes, while still maintaining a seal of the underlying face mask on the face.

In some implementations, the cushion is made from a low durometer material, a medical grade surgical rubber, or a medical grade silicone. In some implementations, the cushion is made from an 'auxetic' material or a material that has a negative Poisson's ratio. In some implementations, the cushion is made from a material having certain material properties, but the segmentation of the cushion into the plurality of flexible projections simulates other material characteristics of a softer material. In some implementations, the flexible projections of the facial cushion simulate the microscopic structure of a material at the macroscopic level to provide a seal on a face of the wearer. In some implementations, the flexible projections are made from a material for which application of a force on a side of the flexible projections perpendicular to the shaped base results in a lengthening of the axial section.

In some implementations, the cushion and the mask brace are formed together in a unitary manufacturing process. For example, the cushion and the mask brace may be co-molded, injection molded, compression molded, thermoformed, or 3D printed together. In some implementations, the cushion is formed separately from the mask brace, such as by 3D printing or by a molding process. The cushion is then affixed to the mask brace, such as by an adhesive or an interlocking joint or other mechanical attachment. In some implementations, the cushion is manufactured on a sleeve which can then be attached to the mask brace. The cushion can be slideably attached to the mask brace, or removably attached to the mask brace.

In another aspect, an elastomeric brace for sealing a face mask to a wearer's face includes a sealing ring, at least one securing strap, and a facial cushion positioned on the sealing ring. The sealing ring has a perimeter that forms an interior opening designed to surround a portion of the face mask when the face mask is placed on the wearer's nose and mouth. The at least one securing strap is attached to the sealing ring by at least one joint region, and secures the sealing ring on the wearer and maintains a seal of the face mask about the nose and the mouth of the wearer. The facial cushion has a plurality of individually flexible projections that extend from a surface of the sealing ring. The plurality of individually flexible projections are positioned between the sealing ring and the wearer's face to improve comfort during use of the mask brace. The plurality of individually flexible projections are able to bend individually to provide a seal of the face mask at a location of the cushion with better fit to the underlying facial topography.

In another aspect, a force-dispersing cushion includes a shaped base and a plurality of flexible projections extending from the shaped base. Each of the plurality of projections has a proximal end that attaches to the shaped base, a distal end opposite the shaped base, and an axial section extending between the proximal and distal ends. Each of the plurality of flexible projections is individually flexible upon application of a force to the shaped base, such that the flexible projections conform to a topography of an underlying surface. The individual flexibility of the projections enable the projections to bend to conform to an underlying topography, while the number of projections maintain a seal over the surface and disperse applied force across multiple points on the surface, lowering the compressive or other force on the surface. The use of flexible projections in forming and maintaining a low-force seal has applications in providing coverings for burns, surgical sites, and other wounds on various parts of the human body, cushions over bruised portions of a body, and areas having broken bones.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout and in which.

DETAILED DESCRIPTION

To provide an overall understanding of the systems, methods, and devices described herein, certain illustrative implementations will be described. While the embodiments described below are described with regard to their use in cushions implemented on braces for securing medical masks, the cushions described herein can be used in combination with other face masks and braces incorporating a filtration system.

Figure 1:
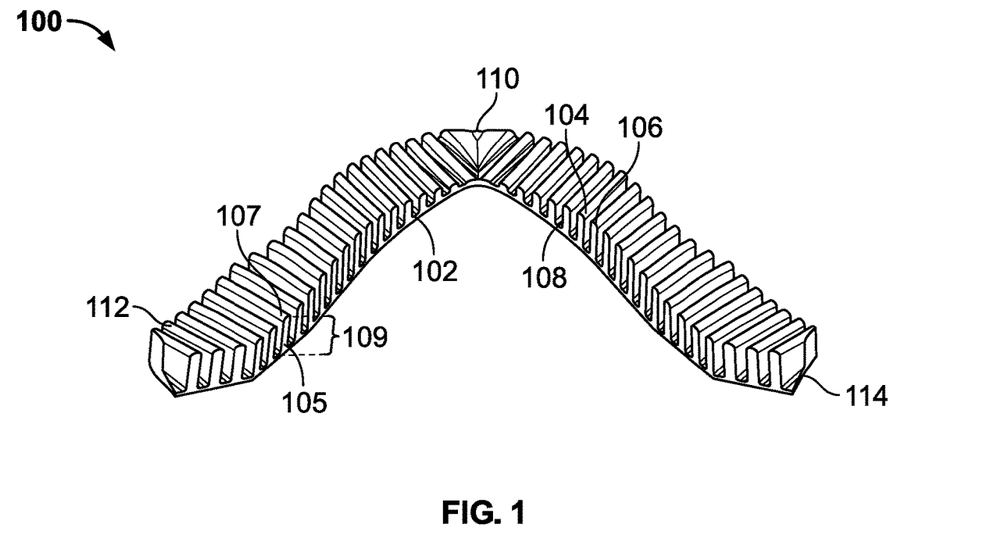
FIG. 1 shows a top-side wireframe drawing of an exemplary cushion.

FIG. 1 shows a top-side wireframe drawing of an exemplary cushion 100. The cushion 100 includes a shaped base 102, and a plurality of flexible projections 104 and 106. The shaped base 102 is shaped as an arch having a first arm 112 and a second arm 114, with a center point 110 where the first arm 112 and second arm 114 meet. The flexible projections 104 and 106 extend outward from the shaped base 102. Though the cushion 100 includes a number of flexible projections, only 104 and 106 are numbered with reference numerals for clarity. The flexible projections 104 and 106 are spaced apart from one another by a space 108.

Each of the flexible projections 104 and 106 are attached to the shaped based 102 at a proximal end 105 and extend away from the shaped base. Each of the flexible projections 104 and 106 have a distal end 107 opposite the shaped base, and an axial section 109 between the proximal end 105 and distal end 107. Each of the flexible projections 104 and 106 are capable of flexing or bending individually upon application of force on the flexible projection. In some implementations, the flexible projections 104 and 106 are capable of deforming upon the application of force.

The flexible projections 104 and 106 may extend orthogonally to the shaped base 102, or can extend from the shaped base 102 at an angle. For example, the flexible projections 104 and 106 can extend from the shaped base 102 at an angle of 20°, 30°, 45°, 50°, 60°, 70°, 80°, or 90°, or at any other suitable angle to the shaped base 102. In some implementations, one or more subsets of flexible projections 104 and 106 extend from the shaped base 102 at a first angle, and a second subset of projections extends from the shaped base 102 at a different second angle. The flexible projections 104 and 106 are spaced apart from one another by a space 108.

The space 108 may be in the range of 0.01 mm to 1 mm, or any suitable distance. The space 108 between the flexible projections 104 and 106 influences the ability of the flexible projections 104 and 106 to bend to conform to the face, where flexible projections that are closely spaced with less distance between them may be inhibited from bending by a neighboring projection, but flexible projections that are spaced far apart may have a decreased ability to form a reliable seal. In some implementations, the space 108 between the flexible projections 104 and 106 may be the same as the spacing between all other flexible projections such that the projections are evenly spaced. In some implementations, the space between flexible projections is variable, or varies across a length of the cushion. Different microscopic properties may be emulated by changing the lengths of flexible projections 104 and 106 and varying the spacing 108 between the projections. While the flexible projections 104 and 106 are illustrated as linear projections which extend straight from the shaped base 102, the flexible projections 104 may be formed to have a shape other than straight. In some implementations, the axial section 109 of the flexible projections 104 and 106 are curved, waved, angled, or bent. In some implementations, a first subset of the flexible projections 104 and 106 are curved, waved, angled, or bent, while second subset are formed to have a straight shape.

Figure 3:
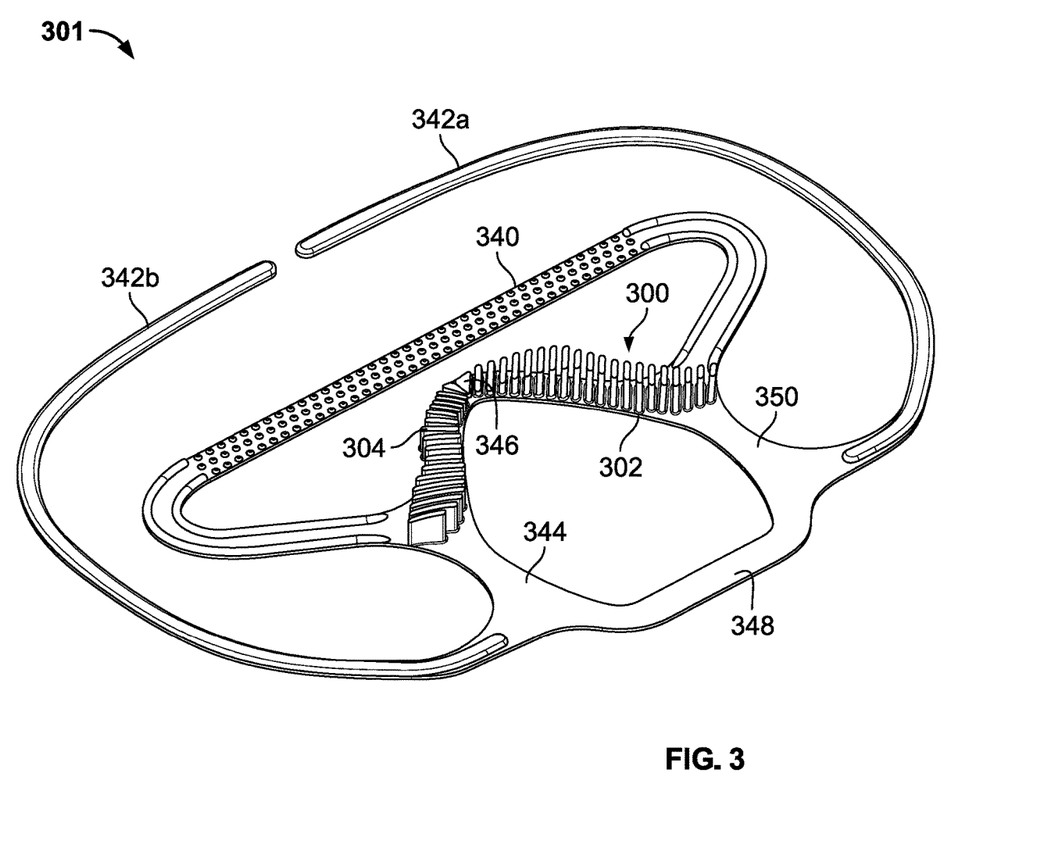
FIG. 3 shows a wireframe drawing of a face mask brace including a nasal cushion.
Figure 4:
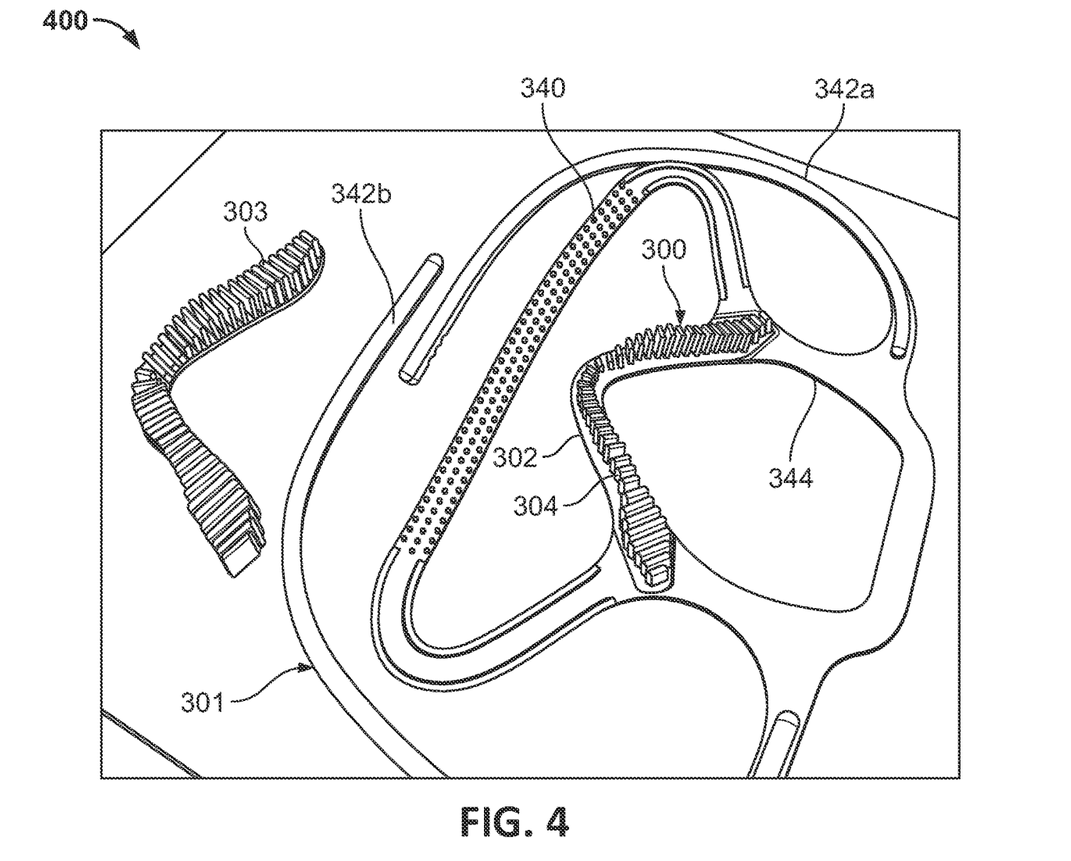
FIG. 4 shows an photo of a nasal cushion and face mask brace including a nasal cushion.

As will be illustrated in FIGS. 3 and 4, the cushion 100 is designed to be placed on a face mask brace used for securing a face mask to a wearer's face. The cushion 100 is located between the face mask brace and a face mask covering the wearer's nose and mouth. The flexibility of the flexible projections 104 and 106 allows the flexible projections 104 and 106 to bend to conform to the shape of underlying facial features and structures. Conforming to the topography of the underlying face provides a more comfortable experience of wearing a mask brace to which the cushion is attached. Because the flexible projections 104 and 106 are individually flexible, the projections still maintain a seal between the brace and the face mask. The seal prevents air from escaping from underneath the face mask around the edges, and also prevents air from entering the mask around the edges. In some implementations, the seal may be air-tight, while in others the seal may alternatively or additionally be water-tight. The flexible projections 104 and 106 enable a face mask brace with a cushion 100 to comfortably and securely fit multiple face shapes, sizes and structures. The cushion 100 distributes the brace tension over the facial structures of the wearer to make wearing the mask brace more comfortable enabling longer periods of wear and better compliance with health and safety requirements to wear a face mask and/or mask brace.

The cushion 100 includes flexible projections 104 and 106 shaped as parallel planes extending from the shaped base 102. This structure is sometimes referred to as a ribbed or ridged structure, a "split finger" structure, mushroom-type ribbing, or vertical struts. The presence of the flexible projections 104 and 106 increases comfort while maintaining a seal, but also may decrease slipping of the brace on the underlying fabric mask. When the cushion 100 is forced against the face mask on a wearer's face by the brace, the flexible projections 104 and 106 bend in one direction or the other, sealing against each other and conforming to the underlying shape of the face. The cushion 100 is shaped for cushioning the nose of a wearer, such that the center line 110 would be at the bridge of the nose. In some implementations, the cushion 100 has other shapes suitable for cushioning other regions of the face or facial structures. For example, the cushion 100 can have a shaped base formed as an oval, rectangle, triangle, or any other suitable shape to provide cushioning to the wearer's cheekbone, jawbone, or chin.

Figure 2:
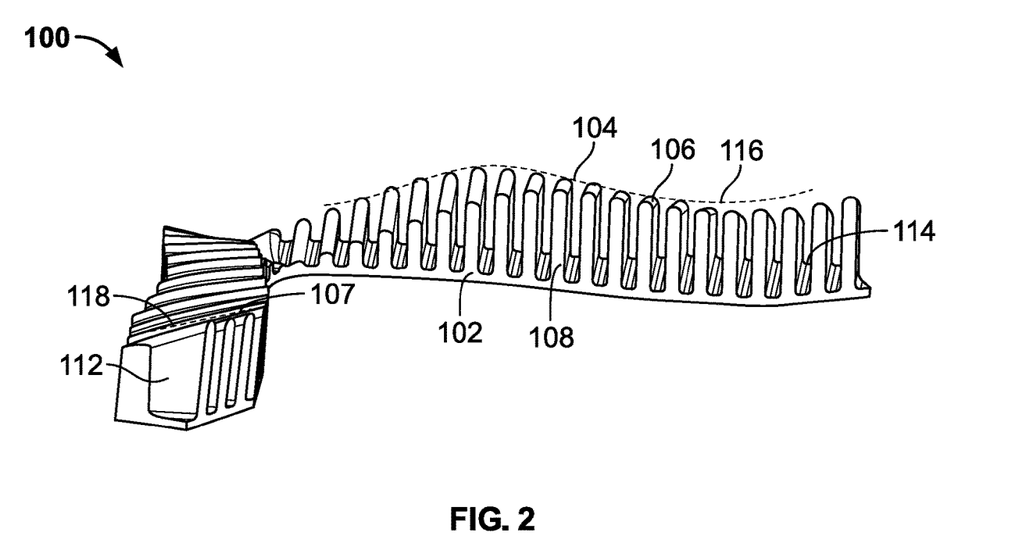
FIG. 2 shows a lateral view wireframe drawing of an exemplary cushion.

The flexible projections 104 and 106 may be formed with varying heights such that a top surface formed by the distal ends of the flexible projections 104 and 106 is contoured. The flexible projections 104 and 106 can have a height in the range of 1 mm to 20 mm, or any suitable height. As illustrated in FIG. 2 which shows a perspective view of the wireframe drawing of the cushion 100, the cushion 100 can have a first contour 116 across the multiple distal ends of the plurality of flexible projections. The varying heights of the flexible projections 104 and 106 create the first contour 116, which extends along the second arm 114 of the cushion 100 in FIG. 2. The cushion 100 can also have a second contour, such as 118, along the top distal end 107 of a single flexible projection. The second contour 118 can be angled, curved, or rounded across the length of the distal end 107. The first contour 116 and second contour 118 together can be made to accommodate the shape of the facial feature that the cushion will be placed over and increase the comfort provided by the cushion 100. The facial feature is further accommodated by the flexing of the flexible projections 104 and 106 when pressure is applied to the cushion 100 by the brace. The flexibility of the individual projections allow the cushion to conform comfortably to accommodate many different topographical surfaces of the wearer's face, such as their nose, and to distribute the force against the face to seal the intermediary face mask without leaking of air or particles around the sides of the mask.

In contrast to a single solid cushion, the cushion 100 with flexible projections 104 and 106 has decreased leakage of gas and particles under the mask brace. Further, the cushion 100 is more comfortable due to better ability to conform to the face. The flexible projections 104 and 106 provide multiple points of contact on the wearer's face rather than the single point of contact provided by a solid cushion, and accordingly create a better seal. Because each of the flexible projections 104 and 106 can flex or bend by itself, the flexible projections 104 and 106 and the cushion 100 have variable contact with the curvature of the face to provide a comfortable seal.

The cushion 100 shown in FIGS. 1 and 2 includes flexible projections 104 and 106 that can individually flex to create distributed contact with the intermediate face mask and underlying facial features for improved comfort while still providing a seal. This allows a wearer to comfortably wear the mask for a longer period of time, increasing compliance with requirements to wear a mask and decreasing risk to the wearer or to others.

While FIGS. 1 and 2 illustrate the use of a plurality of flexible projections 104 and 106 in use as a cushion 100 for use with a face mask brace, the principle of employing multiple individually flexible projections to conform to the topography of a surface of the body, while simultaneously lowering the compressive force on the surface by providing multiple points of contact on the surface and maintaining a seal over the surface is widely applicable. Many medical applications require formation of a water or air-tight low-force seal over a varied surface of the body, and may benefit from the use of a multiple individually flexible projections. For example, cushions including the multiple individually flexible projections can be used in providing water or air-tight coverings or cushions for burns, surgical sites or wounds on any part of the body, or in other medical coverings and cushions such as for areas of a body which are bruised or contain broken bones. For example, a cushion including individually flexible projections can provide a low-force dressing over broken facial bones. The flexible projections of such coverings may be formed from a variety of materials including low durometer materials, medical grade surgical rubber, medical grade silicone, TPU and TPE. In some implementations, the projections may be formed from 'auxetic' material or negative Poisson's ratio materials which expand in the y-direction when pulled in the x-direction, having properties which derive from their structure, not their composition. For a cushion made from such a material, regardless of the surface or surface topography to which it is applied, a force applied to a lateral edge of the flexible projection 104 and 106 would result in a lengthening of the flexible projections 104 and 106, conforming to the underlying topographical structures while maintaining the low-force seal on the surface of the covered body part. The projections can be formed from a material that has certain material properties and characteristics, but the segmentation into the individual flexible projections 104 and 106 simulates material characteristics of a softer material, contacting the surface at multiple points and providing a low-force seal. The flexible projections 104 and 106 can simulate at the macroscopic level the microstructure of a different material, providing a seal on any surface, including a human face or other portion of the human body. Additional applications for providing low-force coverings and cushions to surfaces besides the human body include seals on ships, rafts, or chemical tanks, as well as providing packaging for fragile objects and materials.

While FIGS. 1 and 2 show aspects of the cushion itself, FIG. 3 illustrates the use of the cushion 300 with a face mask brace 301. The face mask brace 301 includes a sealing ring 344, a head strap 340 and a pair of neck ties 342a-b. The cushion 300 includes a shaped base 302 and a plurality of flexible projections 304 extending from the shaped base 302.

The face mask brace 301 sealing ring 344 forms a perimeter around an interior opening. The perimeter of the sealing ring 344 surrounds a portion of the face mask when the face mask is placed about the wearer's nose and mouth. The head strap 340 and neck ties 342a-b are attached to the sealing ring 344 at joint regions (not shown) where the securing strap joins to the sealing ring 344. The head strap 340 and neck ties 342a-b secure the sealing ring 344 to the wearer's face in order to create a seal around the perimeter of the sealing ring 344. The sealing ring 344 includes a nose portion 346 which fits over a wearer's nose, a chin portion 348 which fits under a wearer's chin, and a jaw or cheek portion 350 which fits over the wearer's cheek bone or jaw bone. In some cases, the jaw or cheek portion 350 may coincide with a joint region where a securing strap (such as head strap 340 or one of the pair of neck ties 342a-b) meets the sealing ring 344.

Though the face mask brace 301 is illustrated here with a head strap 340 and a pair of neck ties 342a-b to secure the sealing ring 344 to the wearer's face, other securing straps may be used. For example, ear straps, one or more head straps, head ties, and neck ties may be used in various combinations to secure the sealing mask 344 to the wearer's face. The securing strap exerts a force on the sealing ring 344 to seal the underlying face mask to the wearer's face to prevent air from escaping or entering around the sides of the face mask. In the absence of cushions, the force exerted on the wearer's face may be uncomfortable, especially on boney portions of the face such as the nose and cheekbones. Use of a cushion, such as cushion 300, improves the comfort of wearing the face mask brace 301.

As described above with regard to FIGS. 1 and 2, when the securing strap exerts the force on the sealing ring 344 to provide the face mask seal, the flexible projections 304 of the cushion 300 individually flex or bend to conform to the wearer's face, more evenly and comfortably distributing the force across the facial structures. The cushion 300 is positioned at the nose portion 346 of the sealing ring 344 to distribute the force over the nose and to provide a comfortable wearing experience. In some implementations, the cushion 300 is positioned at the chin region 348, or the jaw or check bone region 344 to provide additional comfort while maintaining a seal. In some implementations, multiple cushions may be positioned about the sealing ring 344. In some implementations, cushions may be positioned on the securing straps such as head strap 340.

In some implementations, the cushion 300 is formed with the face mask brace 301 during a unitary manufacturing process. The cushion 300 and face mask brace 301 can be formed as a single unit by co-molding, injection molding, compression molding, thermoforming, or 3-D printing. When the cushion 300 and the face mask brace 301 are formed together, a portion of the face mask brace 301 can function as the shaped base of the cushion, such that the flexible projections 304 extend from the surface of the face mask brace 301. The cushion 300 and face mask brace 301 can be formed from the same material, such as medical grade surgical rubber, medical grade silicone, or other low durometer material such as TPE or TPU. Forming the cushion 300 and the face mask brace 301 as a single unit facilitates easy cleaning of the face mask brace 301 including the cushion 300. For example, the face mask brace 301 can be cleaned in an autoclave, dishwasher, or sink. The spacing of the flexible projections 304 provide fluid flow through the cushion 300 and aid in the drip drying process. The flexibility of the cushion 300 allows for flexing of the cushion 300 to ensure all surfaces are cleaned.

In some implementations, the cushion 300 is formed separately from the face mask brace 301 and attached to the brace. The cushion 300 can be formed by co-molding, injection molding, compression molding, thermoforming, or 3-D printing. The face mask brace 301 can be formed by die-cutting, co-molding, injection molding, compression molding, thermoforming, or 3-D printing. The cushion 300 can then be affixed to the face mask brace 301 by adhesive, an interlocking joint, or any other suitable means for mechanical attachment. In some implementations, the cushion 300 is formed as part of a sleeve that can be attached to the face mask brace 301 after manufacturing, for example by adhesive, an interlocking joint, by snaps or Velcro on flaps of the sleeve, or other means of mechanical attachment. In some implementations, the cushion 300 can be slideably or removably attached to the face mask brace 301.

The cushion 300 can be formed from a low durometer material such as TPE or TPU, a medical grade surgical rubber, or medical grade silicone. In some implementations, the cushion 300 can also be formed from a material having a negative Poisson's ratio. Negative Poisson ratio materials, or "auxetic" materials expand in the y-direction when pulled in the x-direction, and their properties derive from their structure, not the composition. For a cushion made from such a material, a force applied to a lateral edge of the flexible projection 304 would result in a lengthening of the flexible projection 304, allowing for comfortable conforming to the facial structures while maintaining the seal on the face mask. In some implementations, the cushion 300 is formed from a material that has certain material properties and characteristics, but the segmentation of the cushion 300 into the individual flexible projections 304 simulates material characteristics of a different, softer material. The flexible projections 304 simulate at the macroscopic level the microstructure of a different material, providing a seal on the face of the user while improving wearer comfort. This enables the flexible projections 304 and cushion 300 to be made from the medical grade or other materials of the face mask brace 301 without sacrificing comfort. The use of a soft material for the cushion 300 would add complexity to the manufacturing process and the cleaning process, and could result in concerns about the reliability of the safety and security of the brace in providing a seal of the face mask.

FIG. 4 shows a photo 400 of a nasal cushion 303 next to a face mask brace 301 including a nasal cushion 300. As in the wireframe drawing in FIG. 3, the face mask brace 301 includes a sealing ring 344, head strap 340, neck ties 342a-b, and cushion 300 having a shaped base 302 and flexible projections 304. The cushion 300 is positioned over the nose portion of the sealing ring 344. When the cushion 300 is manufactured together with the face mask brace 301 in a unitary process, the nose portion of the face mask brace 301 may form the shaped base 302 of the cushion 300. FIG. 4 illustrates the ability to manufacture the cushion 303 separately from the face mask brace 301 for later attachment, as well as the ability to manufacture the face mask brace 301 together with the cushion 300 using molding processes. Because of the flexibility of the projections making up the cushion and ability to form to varying topographies, a small number of cushion shapes can be successfully and comfortably used to seal a face mask to a variety of face shapes and sizes.

Figure 5:
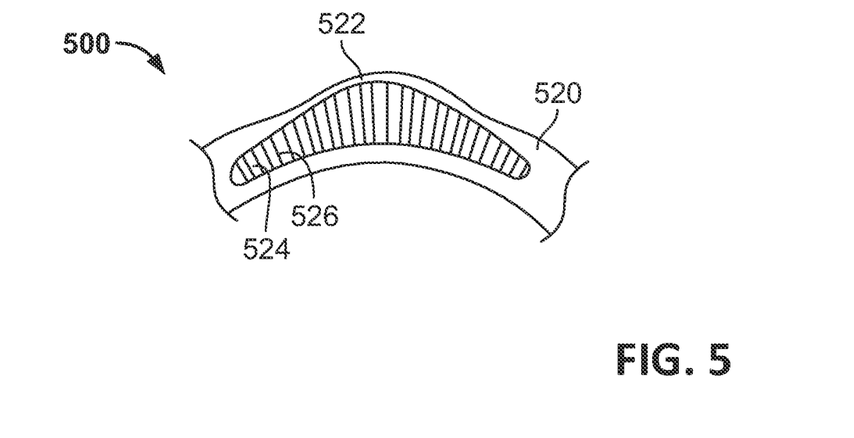
FIG. 5 shows an exemplary cushion including comb-type ribbing.

FIG. 5 shows an exemplary plan view drawing 500 of a cushion 522 including flexible projections 524 and 526 as planar structures. The cushion 522 is positioned on a portion of a sealing ring 520 and includes a first flexible projection 524 and a second flexible projection 526 spaced evenly apart. While only the first flexible projection 524 and second flexible projection 526 are numbered in the drawing, the cushion 522 includes a plurality of projections, and indeed can include any suitable number of projections. In some implementations, the cushion 522 can include 10, 20, 30, 40, 50, or 100 projections, or any suitable number of projections.

First flexible projection 524 and second flexible projection 526 are constructed as planes cut across the cushion 522. Though first flexible projection 524 and second flexible projection 526 are illustrated as extending orthogonally from the cushion 522, the first flexible projection 524 and second flexible projection 526 can extend from the base of the cushion or sealing ring 520 at an angle. For example, the first flexible projection 524 and second flexible projection 526 can extend from the sealing ring 520 at an angle of 20°, 30°, 45°, 50°, 60°, 70°, 80°, or 90°, or at any other suitable angle to the sealing ring 520 or cushion base.

The planes formed by the first flexible projection 524 and second flexible projection 526 are shown as parallel, though they need not be. The planar flexible projections can be evenly spaced, though they need not be and can be variably spaced. The planar flexible projections can similarly be evenly sized, such that the flexible projections have a common width in one direction along the cushion, or they can be variably sized. The planes extend from one edge of the cushion to the other opposite edge, separating the cushion into a plurality of rectangular columns, or substantially rectangular columns that resemble ribs, ridges, or struts from above. The planar projections may resemble the tines of a comb, and may be referred to as a comb-type ribbing. Each projection, for example the first flexible projection 524, may have a constant cross section from a base of the projection to the distal end of the projection, or may have a variable cross section or decreasing cross section from the base to the distal end of the projection. In some implementations, the distal ends of the projections are contoured as described above in FIG. 2.

Figure 6:
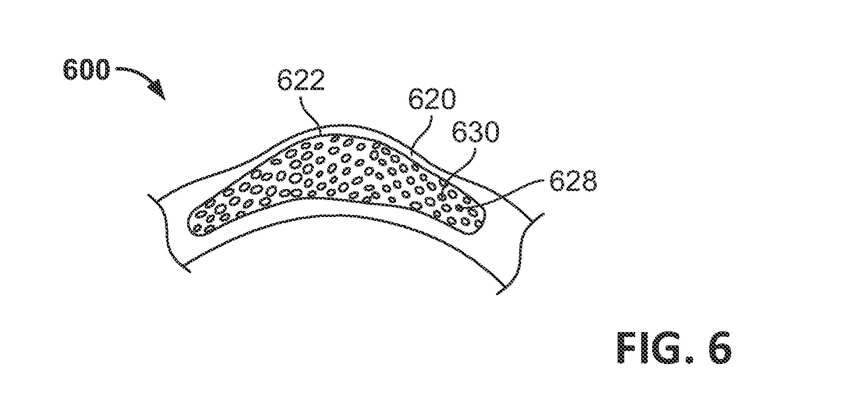
FIG. 6 shows an exemplary cushion including pin-type ribbing.

While FIG. 5 shows a cushion having planar projections, FIG. 6 shows an exemplary plan view drawing 600 of a cushion 622 including pin-type flexible projections 628 and 630. The cushion 622 is positioned on a portion of a sealing ring 620 and includes a first flexible projection 628 and a second flexible projection 630. First flexible projection 628 and second flexible projection 630 are formed as columns, with a width smaller than the distance from a first edge to the opposite edge of the cushion 622. While only the first flexible projection 628 and second flexible projection 630 are numbered in the drawing, the cushion 622 includes a plurality of projections, and indeed can include any suitable number of projections. In some implementations, the cushion 622 can include 30, 40, 50, 75, 100, 125, 150, or 200 projections, or any suitable number of projections. Though first flexible projection 628 and second flexible projection 630 are illustrated as extending orthogonally from the cushion 622, the first flexible projection 628 and second flexible projection 630 can extend from the base of the cushion or sealing ring 620 at an angle. For example, the first flexible projection 628 and second flexible projection 630 can extend from the sealing ring 60 at an angle of 20°, 30°, 45°, 50°, 60°, 70°, 80°, or 90°, or at any other suitable angle to the sealing ring 620 or cushion base.

The columnar projections of the first flexible projection 628 and the second flexible projection 630 are pin-like, and may be referred to as a pin-type ribbing. The columnar projections may resemble the bristles of a hair brush. The projections can have any suitable base shape, such as a triangular or rectangular base, or a circular base as shown, or any other suitable shape. Each projection can have a constant cross-section from the base to the distal end, or can have a variable cross-section. In some implementations, each projection has a cross section which decreases from the base to the distal end. In some implementations, the distal ends of the projections are contoured as described above in FIG. 2. In some implementations, the projections are arranged in lines, rows, and columns across the cushion 622. In some implementations, the projections are arranged randomly. In some implementations, the projections are arranged in a staggered grid-type manner. The arrangement of the projections in a grid may improve the sealing of the face mask brace 620 in the area of the cushion 622 by providing more air resistance and better conforming to the face thereby reducing air leakage under the brace. Fluid flow properties and material usage may be optimized by use of an appropriately staggered pin configuration. In some implementations, the cushion can include both planar type projections of FIG. 5 and pin-type projections of FIG. 6 together.

Figure 7:
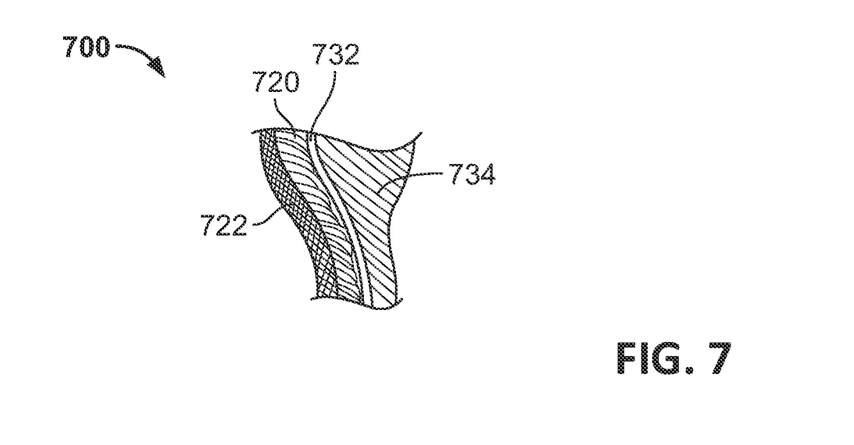
FIG. 7 shows a perspective view of a mask brace with cushion sealing a face mask to a portion of a wearer's face.

FIG. 7 shows a perspective view 700 of a mask brace 722 with cushion 720 sealing a face mask 732 to a portion of a wearer's face 734. FIG. 7 illustrates the way that the cushion 722 is positioned between the face mask brace 722 and the face mask 732 in order to provide a comfortable seal of the face mask 732 on the wearer's face 734. The face mask brace 720 exerts a force on the cushion 722, causing flexible projections of the cushion 722 to flex and bend to conform to the underlying structure of the wearer's face 734. The flexible projections of the cushion 722 push the face mask 732 against the wearer's face 734, providing a seal of the face mask.

By including in the cushion 720 (such as cushion 100 in FIGS. 1 and 2, cushion 300 in FIGS. 3 and 4, cushion 522 in FIG. 5, and cushion 622 in FIG. 6) individually flexible projections (such as flexible projections 104 and 106 in FIGS. 1 and 2, first flexible projection 524 and second flexible projection 526 in FIG. 5, and first flexible projection 628 and second flexible projection 630 in FIG. 6), each projection can flex under the force of the face mask brace 722 to conform to the wearer's underlying facial structure 734, while still maintaining a secure seal of the intermediate face mask 732. A cushion made of multiple flexible projections distributes the force over the facial features with multiple points of contact to improve comfort to the wearer without sacrificing security of the mask seal. The improved comfort to the wearer allows the wearer to continuously wear the mask for long periods of time without adjustment or removal, increasing safety and probability of compliance with regulations requiring the use of a face mask. The use of flexible projections allows for the creation of a few cushion shapes with the capability to comfortably fit a wide range of face sizes, shapes and structures, decreasing the complexity of manufacturing, producing and sourcing comfortable face mask braces. The flexible projections of the cushion can conform to multiple topographies and still maintain the face mask seal.

The foregoing is merely illustrative of the principles of the disclosure, and the apparatuses can be practiced by other than the described implementations, which are presented for purposes of illustration and not of limitation.

Variations and modifications will occur to those of skill in the art after reviewing this disclosure. The disclosed features may be implemented, in any combination and subcombination (including multiple dependent combinations and subcombinations), with one or more other features described herein. For example, any of the facial cushions described above can be positioned on any portion of a face mask or face mask brace to provide comfort during wear and securely seal the face mask to the wearer's face. Any of the facial cushions described above can be constructed with any of the possible cushion designs described above. Any of the facial cushions described above can be practiced with face mask braces that include one or more of ear, head or neck straps, metal bands, or bridges to increase comfort and fit. Accordingly, the various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

ILLUSTRATIVE EMBODIMENTS

Embodiment A

A1. A facial cushion for use with a mask brace that is configured to secure a face mask to a patient's face, the facial cushion comprising:
a shaped base;
a plurality of flexible projections extending from the shaped base, each of the plurality of projections having a proximal end that attaches to the shaped base, a distal end opposite the shaped base, and an axial section extending between the proximal and distal ends;
wherein the plurality of flexible projections can individually flex.

A2. The facial cushion of A1, wherein each of the plurality of flexible projections is formed in a vertical plane extending orthogonally from the shaped base.

A3. The facial cushion of A2, wherein the vertical planes are parallel to one another.

A4. The facial cushion of any of A1-A3, wherein the distal end is contoured.

A5. The facial cushion of any of A1-A4, wherein a contoured shape of the distal end of a first flexible projection differs from a contoured shape of a second flexible projection.

A6. The facial cushion of any of A1-A5, wherein each distal end is angled or curved with respect to a surface of the shaped base.

A7. The facial cushion of any of A1-A6, wherein the contour of the distal ends is symmetric across a center line of the shaped base.

A8. The facial cushion of any of A1-A7, wherein the tip of each of the plurality of flexible projections is formed as a pin.

A9. The facial cushion of any of A1-A8, wherein the proximal end of each of the plurality of flexible projections has a cross section that is circular, triangular, or rectangular.

A10. The facial cushion of A1-A8, wherein the proximal ends of the plurality of flexible projections are arranged in a grid pattern on the shaped base.

A11. The facial cushion of any of A1-A8, wherein the proximal end of each of the plurality of flexible projections has a rectangular cross section extending from a first edge of the shaped base to a second edge of the shaped base opposite the first edge.

A12. The facial cushion of A11, wherein the axial section of each of the plurality of flexible projections is a rectangular column.

A13. The facial cushion of any of A1-A12, wherein each distal end is rounded.

A14. The facial cushion of any of A1-A13, wherein the axial section has a constant cross-section from the shaped base to the distal end.

A15. The facial cushion of any of A1-A13, wherein the axial section decreases in cross-section from the shaped base to the distal end.

A16. The facial cushion of any of A1-A13, wherein the axial section has a variable cross-section from the shaped base to the distal end.

A17. The facial cushion of any of A1-A16, wherein the plurality of flexible projections include at least one pin-type projection and at least one plane-type projection.

A18. The facial cushion of any of A1-A17, wherein the plurality of flexible projections have varying heights.

A19. The facial cushion of any of A1-A18, wherein each of the plurality of flexible projections are spaced apart.

A20. The facial cushion of any of A1-A19, wherein the shaped base comprises an arch shape having two arms.

A21. The facial cushion of any of A1-A20, wherein a contour of the distal ends of the flexible projections is symmetric on both of the two arms.

A22. The facial cushion of any of A1-A20, wherein the shaped base comprises a substantially oval shape.

A23. The facial cushion of any of A1-A20, wherein the shaped base comprises a substantially rectangular shape.

A24. The facial cushion of any of A1-A20, wherein the shaped base comprises a substantially triangular shape.

A25. The facial cushion of any of A1-A24, wherein the shaped base is configured to extend over a nose of a user of the mask brace.

A26. The facial cushion of any of A1-A24, wherein the shaped base is configured to extend over a cheek bone of a user of the mask brace.

A27. The facial cushion of any of A1-A24, wherein the shaped base is configured to extend over a jaw bone of a user of the mask brace.

A28. The facial cushion of any of A1-A27, wherein the facial cushion is configured to extend between the mask brace and a face mask worn by a user of the mask brace.

A29. The facial cushion of any of A1-A28, wherein the facial cushion comprises a low durometer material.

A30. The facial cushion of any of A1-A29, wherein the facial cushion comprises a medical grade surgical rubber.

A31. The facial cushion of any of A1-A29, wherein the facial cushion comprises a medical grade silicone.

A32. The facial cushion of any of A1-A28, wherein the facial cushion comprises a material having a negative Poisson's ratio.

A33. The facial cushion of any of A1-A32, wherein the facial cushion comprises a first material having a structure that simulates material characteristics of a softer material.

A34. The facial cushion of A33, wherein the plurality of flexible projections comprising the facial cushion individually flex such that the facial cushion has material characteristics of a softer material.

A35. The facial cushion of A34, wherein the plurality of flexible projections of the facial cushion simulate the microscopic structure of a material at the macroscopic level to provide a seal on a face of the wearer.

A36. The facial cushion of any of A34 or A35, wherein the flexible projections are configured such that application of a force on a side of the flexible projections perpendicular to the shaped base results in a lengthening of the axial section.

A37. The facial cushion of any of A1-A36, wherein the cushion and the mask brace are configured to be formed in a unitary manufacturing process.

A38. The facial cushion of any of A1-A37, wherein the cushion is configured to be co-molded with the mask brace.

A39. The facial cushion of any of A1-A37, wherein the cushion is configured to be injection molded with the mask brace.

A40. The facial cushion of any of A1-A37, wherein the cushion is configured to be compression molded with the mask brace.

A41. The facial cushion of any of A1-A37, wherein the cushion is configured to be thermoformed with the mask brace.

A42. The facial cushion of any of A1-A37, wherein the cushion is configured to be 3-D printed with the mask brace.

A43. The facial cushion of any of A1-A36, wherein the cushion is configured to be 3-D printed.

A44. The facial cushion of any of A1-A36, wherein the cushion is configured to be molded.

A45. The facial cushion of any of A1-A36, wherein the cushion is configured to be manufactured separately from the mask brace and affixed to the mask brace by an adhesive.

A46. The facial cushion of any of A1-A36, wherein the cushion is configured to be manufactured separately from the mask brace and affixed to the mask brace by an interlocking joint.

A47. The facial cushion of any of A1-A36, wherein the cushion is configured to be manufactured as part of a sleeve separately from the mask brace, and wherein the sleeve is configured to be affixed to the mask brace.

A48. The facial cushion of any of A1-A47, wherein the cushion is positioned on a sealing ring of the mask brace, the sealing ring having a perimeter that forms an interior opening, the perimeter configured to surround a portion of the face mask when the face mask is placed about the wearer's nose and mouth.

A49. The facial cushion of any of A1-A47, wherein the cushion is positioned on a securing strap of the mask brace, the securing strap attached to the sealing ring by at least one joint region.

A50. The facial cushion of any of A1-A47, wherein the cushion is positioned on a joint region of the mask brace, the joint region located where a sealing ring and securing strap of the mask brace join.

Embodiment B

B1. An elastomeric brace for sealing a face mask to a wearer's face, the brace comprising:

a sealing ring having a perimeter that forms an interior opening, the perimeter configured to surround a portion of the face mask when the face mask is placed about the wearer's nose and mouth;

at least one securing strap attached to the sealing ring by at least one joint region; and a facial cushion positioned on the sealing ring, the cushion comprising a plurality of individually flexible projections extending from a surface of the sealing ring;

wherein the securing strap is configured to secure the sealing ring on the wearer and maintain a seal of the face mask about the nose and the mouth of the wearer, and wherein the plurality of individually flexible projections are positioned between the sealing ring and the wearer's face, the plurality of individually flexible projections configured to bend to provide a seal of the face mask at a location of the cushion.

Embodiment C

C1. A method of manufacturing the cushion of any of A1-A33 using a co-molding process.

C2. A method of manufacturing the cushion of any of A1-A33 using an injection molding process.

C3. A method of manufacturing the cushion of any of A1-A33 using a compression molding process.

C4. A method of manufacturing the brace of B1 using a co-molding process.

C5. A method of manufacturing the brace of B1 using an injection molding process.

C6. A method of manufacturing the brace of B1 using a compression molding process.

C7. A method of manufacturing the brace of B1 using a thermoforming process.

C8. A method of manufacturing the brace of B1, the method comprising:

using a die-cutting process to manufacture the sealing ring using a molding process to manufacture the cushion; and adhering the cushion to the sealing ring.

C9. The method of C8, wherein adhering the cushion to the sealing ring comprises:

applying an adhesive to a back side of the cushion; and affixing the cushion on the sealing ring.

C10. The method of C8, wherein adhering the cushion to the sealing ring comprises: stapling the cushion to the sealing ring.

C11. The method of C8, wherein the cushion is manufactured in combination with a sleeve, and wherein adhering the cushion to the sealing ring comprises affixing the sleeve to the sealing ring.

C12. The method of C11, wherein the sleeve is affixed to the sealing ring by an adhesive.

C13. The method of C11, wherein the sleeve is slideably affixed to the sealing ring.

C14. The method of C11, wherein the sleeve is removably affixed to the sealing ring.

C15. The method of any of C8-C14, further comprising:
manufacturing the securing strap with the sealing ring using the die-cutting process.

Embodiment D

D1. A force-dispersing cushion, the cushion comprising:
a shaped base; and
a plurality of flexible projections extending from the shaped base, each of the plurality of projections having a proximal end that attaches to the shaped base, a distal end opposite the shaped base, and an axial section extending between the proximal and distal ends;
wherein each of the plurality of flexible projections is individually flexible upon application of a force to the shaped base, such that the flexible projections conform to a topography of an underlying surface.

D2. The force-dispersing cushion of D1, wherein each of the plurality of flexible projections is formed in a vertical plane extending orthogonally from the shaped base.

D3. The force-dispersing cushion of D1 or D2, wherein the vertical planes are parallel to one another.

D4. The force-dispersing cushion of any of D1-D3, wherein the distal end is contoured.

D5. The force-dispersing cushion of any of D1-D4, wherein a contoured shape of the distal end of a first flexible projection differs from a contoured shape of a second flexible projection.

D6. The force-dispersing cushion of any of D1-D5, wherein each distal end is angled or curved with respect to a surface of the shaped base.

D7. The force-dispersing cushion of any of D1-D6, wherein the contour of the distal ends is symmetric across a center line of the shaped base.

D8. The force-dispersing cushion of any of D1-D7, wherein the tip of each of the plurality of flexible projections is formed as a pin.

D9. The force-dispersing cushion of any of D1-D8, wherein the proximal end of each of the plurality of flexible projections has a cross section that is circular, triangular, or rectangular.

D10. The force-dispersing cushion of D1-D8, wherein the proximal ends of the plurality of flexible projections are arranged in a grid pattern on the shaped base.

D11. The force-dispersing cushion of any of D1-D8, wherein the proximal end of each of the plurality of flexible projections has a rectangular cross section extending from a first edge of the shaped base to a second edge of the shaped base opposite the first edge.

D12. The force-dispersing cushion of D11, wherein the axial section of each of the plurality of flexible projections is a rectangular column.

D13. The force-dispersing cushion of any of D1-D12, wherein each distal end is rounded.

D14. The force-dispersing cushion of any of D1-D13, wherein the axial section has a constant cross-section from the shaped base to the distal end.

D15. The force-dispersing cushion of any of D1-D13, wherein the axial section decreases in cross-section from the shaped base to the distal end.

D16. The force-dispersing cushion of any of D1-D13, wherein the axial section has a variable cross-section from the shaped base to the distal end.

D17. The force-dispersing cushion of any of D1-D16, wherein the plurality of flexible projections include at least one pin-type projection and at least one plane-type projection.

D18. The force-dispersing cushion of any of D1-D17, wherein the plurality of flexible projections have varying heights.

D19. The force-dispersing cushion of any of D1-D18, wherein each of the plurality of flexible projections are spaced apart.

D20. The force-dispersing cushion of any of D1-D19, wherein the force-dispersing cushion is configured to extend over a variable topography surface.

D21. The force-dispersing cushion of any of D1-D20, wherein the force-dispersing cushion comprises a low durometer material.

D22. The force-dispersing cushion of any of D1-D20, wherein the force-dispersing cushion comprises a medical grade surgical rubber.

D23. The force-dispersing cushion of any of D1-D20, wherein the force-dispersing cushion comprises a medical grade silicone.

D24. The force-dispersing cushion of any of D1-D20, wherein the force-dispersing cushion comprises a material having a negative Poisson's ratio.

D25. The force-dispersing cushion of any of D1-D20, wherein the force-dispersing cushion comprises a first material having a structure that simulates material characteristics of a softer material.

D26. The force-dispersing cushion of D25, wherein the plurality of flexible projections comprising the force-dispersing cushion individually flex such that the force-dispersing cushion has material characteristics of a softer material.

D27. The force-dispersing cushion of D26, wherein the plurality of flexible projections of the force-dispersing cushion simulate the microscopic structure of a material at the macroscopic level to provide a seal over a variable topography.

D28. The force-dispersing cushion of any of D26 or D27, wherein the flexible projections are configured such that application of a force on a side of the flexible projections perpendicular to the shaped base results in a lengthening of the axial section.

D29. The force-dispersing cushion of any of D1-D28, wherein the force-dispersing cushion is configured to be 3-D printed.

D30. The force-dispersing cushion of any of D1-D28, wherein the force-dispersing cushion is configured to be molded.

D31. The force-dispersing cushion of any of D1-D30, wherein the force-dispersing cushion is configured to provide an air-tight seal over a wound on a portion of a human body.

D32. The force-dispersing cushion of any of D1-D30, wherein the force-dispersing cushion is configured to provide an air-tight seal over a burn on a portion of a human body.

D33. The force-dispersing cushion of any of D1-D30, wherein the force-dispersing cushion is configured to provide a water-tight seal over a surgical site on a portion of a human body.

D34. The force-dispersing cushion of any of D1-D30, wherein the force-dispersing cushion is configured to provide a cushion over a bruised region of a human body or a region of a human body having a broken bone.

D35. The force-dispersing cushion of any of D1-D30, wherein the force-dispersing cushion is configured to provide a packaging for an object.

We claim:

1. A facial cushion for use with a mask brace that is configured to secure a face mask worn over a nose and a mouth of a wearer against the wearer's face for filtering air being inhaled by the wearer, the facial cushion comprising:
    a shaped base; and
    a plurality of flexible projections extending from the shaped base, each of the plurality of projections having a proximal end that attaches to the shaped base, a distal end opposite the shaped base, and an axial section extending between the proximal and distal ends;
    wherein the plurality of flexible projections can individually flex;
    wherein the plurality of flexible projections are configured to extend between the shaped base and the face mask to hold the face mask in place over the nose and mouth of the wearer; and
    wherein the facial cushion is configured to extend between the mask brace and the face mask.

2. The facial cushion of claim 1, wherein each of the plurality of flexible projections is formed in a vertical plane extending orthogonally from the shaped base.

3. The facial cushion of claim 2, wherein the vertical planes are parallel to one another.

4. The facial cushion of claim 1, wherein the distal end of each of the plurality of projections comprises a contoured shape.

5. The facial cushion of claim 4, wherein the contoured shape of the distal end of a first flexible projection differs from the contoured shape of a second flexible projection.

6. The facial cushion of claim 4, wherein the distal end of each of the plurality of projections is angled or curved with respect to a surface of the shaped base.

7. The facial cushion of claim 4, wherein the contoured shape of the distal ends is symmetric across a center line of the shaped base.

8. The facial cushion of claim 1, wherein the proximal end of each of the plurality of flexible projections comprises a cross section having one of a circular, a triangular, and a rectangular shape.

9. The facial cushion of claim 1, wherein the proximal ends of the plurality of flexible projections are arranged in a grid pattern on the shaped base.

10. The facial cushion of claim 1, wherein the axial section of each of the plurality of flexible projections is a rectangular column.

11. The facial cushion of claim 1, wherein the axial section of each of the plurality of flexible projections has a constant cross-section from the shaped base to the distal end.

12. The facial cushion of claim 1, wherein the axial section of each of the plurality of flexible projections has a variable cross-section from the shaped base to the distal end.

13. The facial cushion of claim 1, wherein the plurality of flexible projections include at least one pin-type projection and at least one plane-type projection.

14. The facial cushion of claim 1, wherein the plurality of flexible projections have varying heights.

15. The facial cushion of claim 1, wherein each of the plurality of flexible projections are spaced apart.

16. The facial cushion of claim 1, wherein the shaped base comprises an arch shape having two arms.

17. The facial cushion of claim 16, wherein a contour of the distal ends of the flexible projections is symmetric on both of the two arms.

18. The facial cushion of claim 17, wherein the shaped base is configured to extend over a nose of a user of the mask brace.

19. The facial cushion of claim 1, wherein the shaped base is configured to extend over a cheek bone of a user of the mask brace.

20. The facial cushion of claim 1, wherein the shaped base is configured to extend over a jaw bone of a user of the mask brace.

21. The facial cushion of claim 1, wherein the facial cushion comprises one of TPE, TPU and silicone.

22. The facial cushion of claim 1, wherein the facial cushion comprises a material having a negative Poisson's ratio, the material being configured to expand vertically between the mask brace and the face mask to increase conformance of the facial cushion to the wearer's face.

23. The facial cushion of claim 1, wherein the facial cushion comprises a first material that simulates material characteristics of a softer material.

24. The facial cushion of claim 23, wherein the plurality of flexible projections of the facial cushion individually flex such that the facial cushion has material characteristics of a softer material.

25. The facial cushion of claim 24, wherein the plurality of flexible projections of the facial cushion simulate the microscopic structure of a material at the macroscopic level to provide a seal of the face mask on a face of the wearer.

26. The facial cushion of claim 24, wherein the flexible projections are configured such that application of a force on a side of the flexible projections perpendicular to the shaped base results in a lengthening of the axial section.

27. The facial cushion of claim 1, wherein the facial cushion is configured to be formed in a unitary manufacturing process with the mask brace.

28. The facial cushion of claim 1, wherein the facial cushion is configured to be positioned on a sealing ring of the mask brace, the sealing ring having a perimeter that forms an interior opening, the perimeter configured to surround a portion of the face mask when the face mask is placed about the wearer's nose and mouth.

29. The facial cushion of claim 28, wherein the facial cushion is configured to be positioned on a joint region of the mask brace, the joint region located where the sealing ring and a securing strap of the mask brace join.

* * * * *